United States Patent [19]

Machek

[11] Patent Number: 4,779,628
[45] Date of Patent: Oct. 25, 1988

[54] GUIDEWIRE ASSEMBLY HAVING MOVEABLE CORE AND LOW PROFILE SAFETY WIRE

[75] Inventor: James E. Machek, Valencia, Pa.

[73] Assignee: Medrad, Inc., Pittsburgh, Pa.

[21] Appl. No.: 61,146

[22] Filed: Jun. 12, 1987

[51] Int. Cl.$^4$ ................................................ A61B 5/00
[52] U.S. Cl. .................................... 128/772; 128/657; 604/95
[58] Field of Search ........................ 128/4–8, 128/656–658, 772; 604/95, 164, 170, 171, 280, 282

[56] References Cited

U.S. PATENT DOCUMENTS

| | | | |
|---|---|---|---|
| 3,521,620 | 7/1970 | Cook | 128/772 |
| 3,528,406 | 9/1970 | Jekel | 128/772 |
| 3,547,103 | 12/1970 | Cook | 604/95 |
| 3,749,086 | 7/1973 | Kline et al. | 128/772 |
| 3,802,440 | 4/1974 | Salem et al. | 128/772 |
| 4,080,706 | 3/1978 | Heilman et al. | |
| 4,538,622 | 9/1985 | Samson et al. | 128/657 |
| 4,548,206 | 10/1985 | Osborne | |

*Primary Examiner*—Max Hindenburg
*Attorney, Agent, or Firm*—Fleit, Jacobson, Cohn & Price

[57] ABSTRACT

A catheter guidewire assembly having a moveable core wire and a safety wire. The safety wire has the cross section of a segment of a circle, such that its curved surface conforms to the inside surface of the guidewire casing.

12 Claims, 1 Drawing Sheet

GUIDEWIRE ASSEMBLY HAVING MOVEABLE CORE AND LOW PROFILE SAFETY WIRE

BACKGROUND OF THE INVENTION

The present invention relates to moveable core guidewires, and more particularly relates to guidewires having safety wires therein.

In medical procedures such as angiography, catheters must be positioned deep in the vascular system, and often such catheters must reach difficult to access regions. In order to introduce such a catheter into the vascular system of a patient, a sharp cannula is inserted through the skin and into the vascular system, and then a spring guide wire is inserted through the cannula and advanced in the vascular system until its distal end reaches the location where the catheter tip is desired. The cannula is then removed from the patient's body and the catheter is inserted into the body by sliding over the guidewire. The guidewire generally then is withdrawn, and the catheter is ready for use. Catheters are also used in non-vascular procedures such as urinary tract procedures, and are introduced as described above, with the aid of the catheter guidewire.

As used herein, the terms "catheter" and "guidewire" are meant to encompass all types of catheters and guidewires. For convenience, however, the specific examples discussed herein relate to procedures dealing with the vascular system. Nevertheless, the present invention is not limited to catheters and guidewires designed for the vascular system, and the benefits and advantages of the present invention apply equally to any medical procedure where a catheter must be introduced through the skin and reach a remote location in the human body.

The specific type of guidewire forming the present invention is the moveable core guidewire. This type of guidewire generally is more flexible and steerable than the fixed core guidewire, and hence can be used in the more difficult to reach locations of the body.

The core wire of the moveable guidewire assembly provides a degree of strength, rigidity, and steerability such that the entire assembly can negotiate the vascular system. And it is known that the flexibility of the guidewire assembly can be altered by changing the flexibility of the core wire along the length thereof. Furthermore, with the moveable core guidewire, the flexibility of the guidewire assembly at the tip can be altered by moving the core wire into and out of the guidewire's distal end.

Structural integrity is another requisite for a successful guidewire. A broken guidewire, with the possibility of leaving debris in the patient's body, cannot be tolerated. A commonly employed precaution against leaving a broken guidewire tip in the vascular system of a patient, is the provision of a thin wire, termed a safety wire, inside the wound outer guidewire casing. The safety wire is customarily connected both to the proximate and distal ends of the guidewire to enable the removal of any broken fragments should a break occur in the outer spring of the guidewire assembly.

Some guidewire assemblies use a safety wire having a circular cross section, while others use a safety wire having a rectangular cross section. In both types of guidewire assemblies, the mere presence of the safety wire makes movement of the core wire more difficult.

Ideally, the safety wire should occupy the least amount of area in the guidewire assembly, for the more room the core wire has inside the guidewire assembly, the easier it is to manipulate the core wire by the medical personnel. Yet, in all the known prior art moveable core guidewires, the safety wire produces dead space, or wasted space, that cannot be used by the moveable core wire.

The moveable core guidewire assembly of the present invention utilizes a safety wire that overcomes the above drawback.

OBJECTS OF THE INVENTION

An object of the present invention is to eliminate the dead space or wasted space, in a moveable core guidewire assembly.

Another object of the present invention is to increase the maneuverability of the core wire inside a guidewire assembly.

Still a further object of the present invention is to increase the available space for the core wire in a moveable core guidewire assembly for easier manipulation by the medical personnel in control of the guidewire assembly.

Another object of the present invention is to provide a moveable core guidewire assembly with a low profile safety wire so as to facilitate movement of the core wire in the guidewire casing, yet without sacrificing the strentth of the safety wire or the structural integrity of the guidewire assembly.

These and other objects of the invention will become apparent when reference is made to the following description and the accompanying drawings.

SUMMARY OF THE INVENTION

Briefly stated, the present invention relates to a moveable core guidewire assembly having a separate low profile safety wire for ensuring structural integrity of the guidewire while providing improved maneuverability of the core wire.

The low profile safety wire extends longitudinally through the guidewire casing and is attached to the casing at the distal and proximal ends thereof.

The cross-sectional shape of the safety wire is a segment of a circle, where the arcuate surface lies immediately adjacent the inner surface of the guidewire casing, and has substantially the same profile as the casing. Such a low profile safety wire can have the same cross-sectional area, and hence strength, as the prior art circular or rectangular safety wires, and yet provide more area within the guidewire casing for the moveable core.

DESCRIPTION OF THE PREFERRED EMBODIMENT

Figure 1:
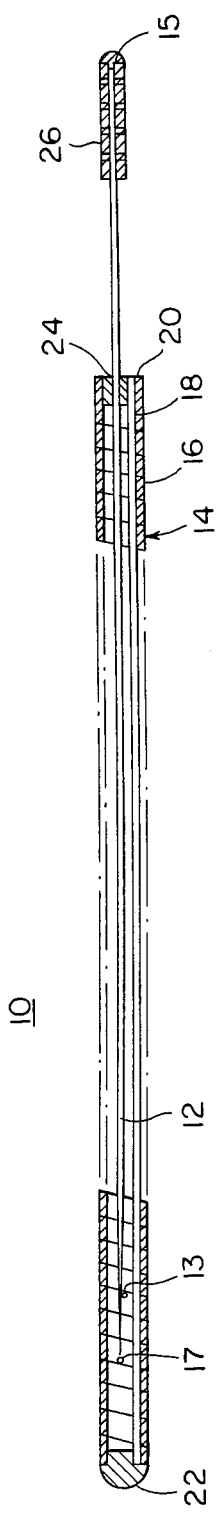
FIG. 1 illustrates a catheter guidewire assembly with a partially withdrawn, moveable core wire and a safety wire.

The present invention relates to a moveable core catheter guidewire assembly and particularly relates to a low profile safety wire connected in the guidewire assembly. FIG. 1 is a partial, longitudinal cross-sectional view of a catheter guidewire assembly 10 in accordance with the preferred embodiment of the present invention. Particularly, the catheter guidewire assembly 10 includes a core wire 12 moveable in a casing assembly 14.

The casing assembly 14 includes a wound outer casing 16 and a safety wire 18 affixed to the proximal end 20 and the distal end 22 of the outer casing 16. The wound outer casing 16 takes the form of a coil spring which is developed from a wound wire, such as a rectangular cross section flat wire. The outer and inner surfaces of casing 16 can be ultra smooth surfaces developed by coating the base flat wire with a lubricating agent, such as Teflon, prior to being spring wound. In this manner, flaking of the outer coating is minimized during bending of the guidewire when in use. Also, the surface of the casing can be lightly ground by abrasion and subsequently electro-polished. A further description of specific casing assemblies can be found in U.S. Pat. No. 4,003,369 by Heilman et al, assigned to the assignee of the present invention, and incorporated herein by reference thereto.

The outer casing 16 of the guide wire assembly 10 is very flexible; therefore, to provide the desired degree of rigidity and steerability, the core wire 12 is inserted into an open end 24 at proximal end 20 of a casing assembly 14. By manipulating core wire 12, the catheter guidewire assembly 10 can negotiate the tortuous path through the vascular system, or other systems, of the patient. The degree of rigidity of the guidewire assembly 10 is primarily dependent upon the rigidity or flexibility of core wire 12.

Core wire 12 includes, at is proximal end 15, a cylindrical handle 26 such that the medical personnel can insert, withdraw and twist the core wire 12 relative to casing 16 of the guidewire assembly 10. The distal end of core wire 12 is tapered, as shown at 13, to provide more flexibility at the distal tip than over the remainder of its length, and is provided with an enlarged tip 17 to prevent the core wire from exiting the casing 16 of the guidewire assembly 10. It is contemplated that the core wire 12 be either straight throughout its length or include a curved section at its distal end to facilitate steering; and core wire 12 can be coated with a lubricating agent, such as Teflon, to facilitate its smooth movement within casing 16.

The length of safety wire 18, as shown in FIG. 1, is substantially the same as the length of the casing 16, and the safety wire 18 is securely attached at ends 20 and 22 of casing 16 so that the possibility of the core wire 12 sliding between the casing 16 and the safety wire 18 is minimized. The safety wire 18 also may be coated with a lubricating agent, such as Telfon.

Although the dimensions of the moveable core guidewire assembly 10 will vary depending upon its intended use, typical dimensions of a guidewire assembly for use in angiography are as follows. The outside diameter of casing 16 is on the order of 0.025 to 0.038 inches, with the casing made from rectangular wire so that the inside diameter is on the order of 0.018 to 0.027 inches. The diameter of the core wire 12 over the major portion of its length is on the order of 0.011 to 0.017 inches, and the cross-sectional area of the typical prior art safety wire (such as rectangular safety wire 18' illustrated in FIG. 2a) is on the order of 0.003×0.010 to 0.003×0.012 inches.

Figure 2C:
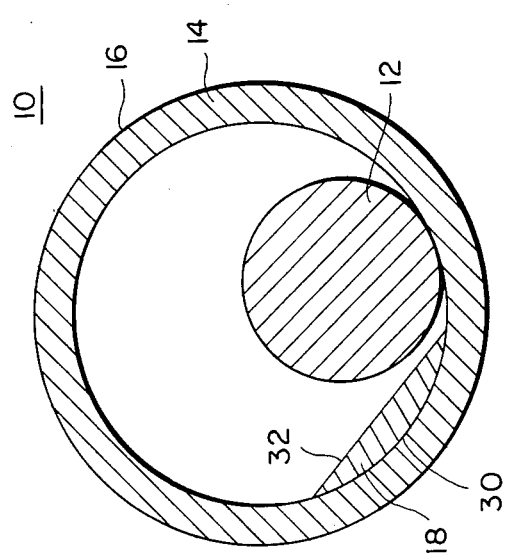
FIG. 2c is a cross section of the guidewire assembly of the present invention.
Figure 2B:
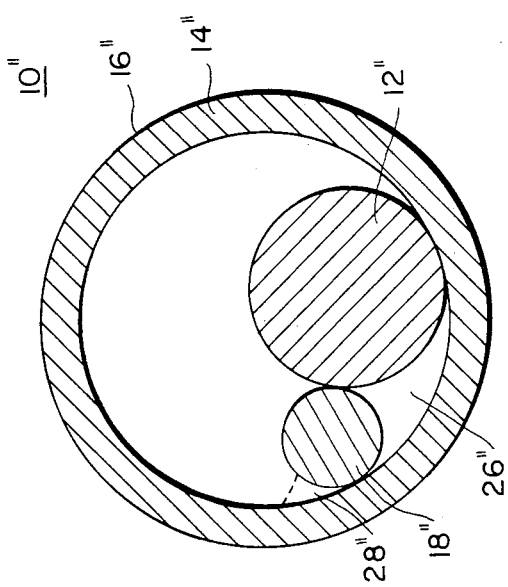
FIG. 2b is a cross section of a prior art guidewire assembly with a safety wire having a circular cross-sectional shape.
Figure 2A:
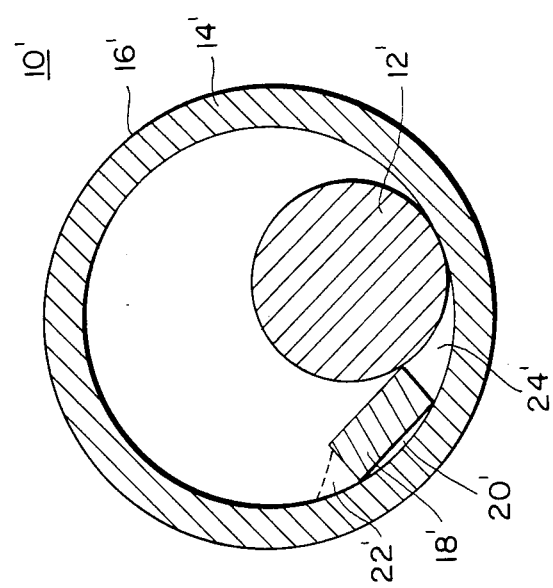
FIG. 2a is a cross section of a prior art guidewire assembly with a safety wire having a rectangular cross-sectional shape.

With reference now to FIGS. 2a, 2b and 2c, the low profile safety wire 18 of the present invention will be described.

FIG. 2a shows one prior art guidewire assembly 10 with a safety wire 18'. having a rectangular cross section. As can be seen from the figure, there exist regions 20', 22' and 24', which are not available to the core wire 12' because they are shielded by the safety wire 18'. These regions are dead, or wasted, space, and hence the movement and maneuverability of the core wire 12' are restricted.

As can be seen in FIG. 2b, similar regions 26" and 28" of wasted or dead space exist when safety wire 18" has a circular cross section as also found in the prior art. Again, therefore, the movement and manenverability of core wire 12" are sacrificed.

FIG. 2c illustrates the low profile safety wire 18 of the present invention which overcomes the drawbacks of the prior art. Specifically, the present invention eliminates the wasted or dead space encountered in the prior art with a safety wire of the same cross-sectional area as that of the prior art. This is accomplished, as shown in FIG. 2c, by shaping safety wire 18 so that the surface 30 adjacent the casing 16 conforms to the curveture or profile of the casing. The opposite surface 32, in the preferred embodiment, is flat. It is contemplated, however that surface 32 may be either concave or convex.

With the low profile safety wire 18 of the present invention, as can be seen when contrasting FIGS. 2a, 2b and 2c, the dead, or wasted spaces are eliminated. The core wire 12 has more room to slide and maneuver inside the casing assembly 14 even though the cross-sectional area (and hence strength) of the inventive low profile safety wire 18 is the same as that of rectangular safety wire 18'. or round safety wire 18". Thus, the medical personnel has an increased ability to manipulate the guidewire assembly 10 in the patient's body.

While only certain preferred features of the present invention have been shown by way of illustration, many modifications and changes can be made without departing from the spirit or scope of the invention. Therefore, it is to be understood that the appended claims are intended to cover all such modifications and changes as are within the true spirit and scope of the invention.

What is claimed is:

1. A moveable core catheter guidewire assembly to be guided through the vascular system of the body comprising:

an elongated wound wire cylindrical casing having a distal closed end and a proximal open end;

an elongated resilient core wire positioned in said cylindrical casing, having a distal end positioned at the distal end of said casing, and having a proximal end extending outside said proximal open end of said casing;

an elongated resilient safety wire having the substantially same length as said cylindrical casing, one end of the safety wire being attached to the distal closed end of the cylindrical casing and the other end of the safety wire being attached to the proximal open end of the cylindrical casing;

said safety wire having the cross section of a segment of a circle along its entire length, with the curved surface thereof conforming to the inside surface of said cylindrical casing, and said curved surface being mounted in contact with said inside surface of said cylindrical casing, thereby providing greater space within said cylindrical casing for said core wire to provide greater flexibility of said guidewire assembly.

2. The moveable core catheter guidewire assembly of claim 1, wherein said cylindrical casing is coated with a lubricating agent on the inner and outer surfaces thereof.

3. The moveable core catheter guidewire assembly of claim 1, wherein said safety wire is coated with a lubricating agent.

4. The moveable core catheter guidewire assembly of claim 1, wherein said core wire is coated with a lubricating agent.

5. A moveable core catheter guidewire assembly to be guided through the vascular system of the body comprising:
 an elongated cylindrical casing having a distal closed end and a proximal open end;
 an elongated core wire moveably positioned in the cylindrical casing;
 a safety wire positioned in the cylindrical casing and attached thereto at the distal and proximal ends thereof, said safety wire having a length substantially the same as that of said cylindrical casing and having a cross section of a segment of a circle along its entire length, the curved surface of said segment conforms to and lies in contact with the inner surface of said cylindrical casing, thereby providing greater space within said cylindrical casing for said core wire to provide greater flexibility of said guidewire assembly.

6. The assembly of claim 5, and further comprising a lubricating agent between the moveable core and the cylindrical casing.

7. The assembly of claim 6, wherein said cylindrical casing is developed from contacting coils of a continuous wound wire.

8. The assembly of claim 7, wherein said lubricating agent completely coats said continuous wound wire.

9. The assembly of claim 5, wherein the distal end of said cylindrical casing is closed.

10. The assembly of claim 5, wherein the surface of said safety wire opposite said curved surface thereof is flat.

11. The assembly of claim 5, wherein the end of said core wire nearest the distal end of said cylindrical casing is 12. The assembly of claim 5, wherein said cylindrical casing is developed from contacting coils of a continuous wound wire.

* * * * *